United States Patent
Su et al.

(10) Patent No.: US 9,033,892 B2
(45) Date of Patent: May 19, 2015

(54) PREDICTIVE DROWSINESS ALARM METHOD

(75) Inventors: Yu Jen Su, Kaohsiung (TW); Yen Hsien Lee, Taoyuan County (TW); Kuang I Chang, Taoyuan County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 462 days.

(21) Appl. No.: 13/245,205

(22) Filed: Sep. 26, 2011

(65) Prior Publication Data

US 2012/0296226 A1 Nov. 22, 2012

(30) Foreign Application Priority Data

May 17, 2011 (TW) .............................. 100117152 A

(51) Int. Cl.
*A61B 5/02* (2006.01)
*A61B 5/024* (2006.01)
*A61B 5/18* (2006.01)
(Continued)

(52) U.S. Cl.
CPC .............. *A61B 5/024* (2013.01); *A61B 5/02405* (2013.01); *A61B 5/18* (2013.01); *G08B 21/06* (2013.01); *G08B 31/00* (2013.01)

(58) Field of Classification Search
CPC ...... A61B 5/18; A61B 5/024; A61B 5/02405; G08B 21/06; G08B 31/00
USPC .......................................... 600/516, 508, 519
See application file for complete search history.

(56) References Cited

U.S. PATENT DOCUMENTS

| | | |
|---|---|---|
| 5,666,959 A | 9/1997 | Deans et al. |
| 6,070,098 A | 5/2000 | Moore-Ede et al. |
| 6,575,902 B1 | 6/2003 | Burton |

(Continued)

FOREIGN PATENT DOCUMENTS

| | | |
|---|---|---|
| CN | 101496716 | 8/2009 |
| TW | 201025207 | 7/2010 |
| WO | 2004091709 | 10/2004 |

OTHER PUBLICATIONS

H.De Rosario, J.S.Solaz, N. Rodriguez, and L.M.Bergasa, "Controlled inducement and measurement of drowsiness in a driving simulator" IET Intelligent Transport Systems, vol. 4, Iss.4, p. 280-288, Dec. 2010.

(Continued)

*Primary Examiner* — Michael Kahelin
*Assistant Examiner* — Mallika D Fairchild
(74) *Attorney, Agent, or Firm* — WPAT, P.C.; Anthony King; Kay Yang

(57) ABSTRACT

A method for predicting drowsiness is disclosed. By obtaining average heart beat rate values of a driver, and according to the characteristics of the heart beat rate values over a period of time, the method is utilized to determine whether the human being is going to sleep. The method comprises the following steps: detecting a heart beat rate of a driver; calculating a curve of the heart beat rate average during a time interval of X minutes; determining an accumulated length of duration during which the calculated linear regression slope values are smaller than the predetermined slope value Z; determining whether the accumulated length of duration is greater than a time threshold T to generate a drowsiness detecting result; and determining whether to raise an alarm based on the drowsiness detecting result.

12 Claims, 8 Drawing Sheets

(51) Int. Cl.
  *G08B 21/06* (2006.01)
  *G08B 31/00* (2006.01)

(56) References Cited

U.S. PATENT DOCUMENTS

| | | |
|---|---|---|
| 7,088,250 B2 | 8/2006 | Yasushi |
| 7,254,439 B2 | 8/2007 | Misczynski et al. |
| 7,839,292 B2 | 11/2010 | Wang et al. |
| 7,970,459 B2 * | 6/2011 | Karasudani .................... 600/509 |
| 8,311,621 B2 * | 11/2012 | Hatakeyama ................... 600/519 |
| 2009/0209829 A1 | 8/2009 | Yanagidaira et al. |
| 2009/0318776 A1 | 12/2009 | Toda et al. |
| 2009/0326399 A1 | 12/2009 | Barrero Batalloso et al. |

OTHER PUBLICATIONS

E.Rogado, J.L. Garcia, R.Barea, L.M.Bergasa and E.Lopez, "Driver fatigue detection system", International Conference on Robotics and Biomimetics, p. 1105-1110, Feb. 21, 2009-Feb. 26, 2009.

Mao, Zhe; Yan, Xin-Ping; Wu, and Chao-Zhong, "Driving fatigue identification method based on physiological signals", Proceedings of the 7th International Conference of Chinese Transportation Professionals Congress 2007 p. 341-351.

S.Milosevic, "Drivers' fatigue studies", Ergonomics, v 40, n 3, p. 381-389, Mar. 1997.

Office Action for TW counterpart application No. 100117152 dated Sep. 11, 2013 citing: WO 2004/091709, CN 101496716, US 5666959, and TW 201025207.

\* cited by examiner

PREDICTIVE DROWSINESS ALARM METHOD

TECHNICAL FIELD

The disclosure relates to a predictive drowsiness alarm method.

BACKGROUND

While driving long distances, drivers must remain focused for lengthy periods of time and can easily become very tired or even fall asleep. During early stages of drowsiness, the driver may fall asleep for brief moments. Attention lapses and reduced alertness occur for short periods (less than 30 seconds) but the driver usually awakens with an awareness of danger. However, the driver subsequently feels weary, and continues to drift in and out of consciousness until finally falling completely asleep. In addition, persons working under highly dangerous conditions in quiet environments, e.g., analysts dealing with dangerous materials requiring focused attention, are likely to become lethargic in a short time. People who become drowsy while working under such conditions may easily lose awareness of the dangers in their surroundings.

U.S. Pat. No. 7,088,250 discloses a fatigue-level estimation apparatus to determine a fatigue level of a driver. U.S. Pat. No. 6,070,098 utilizes an observation of activities related to fatigue and determines a level of fatigue based on a large amount of processed data. However, the detected data of a drowsy driver, such as observations of a driver's behavior or the reflectivity of the eyelid, may be similar to those of an alert subject. Therefore, there is a need to reduce required data processing amount and to detect drowsiness effectively, so as to meet industrial requirements.

SUMMARY

The present disclosure provides a predictive drowsiness alarm method, which detects drowsiness of a driver in accordance with heart beat rates over multiple time intervals.

The present disclosure provides a predictive drowsiness alarm method comprising the following steps: detecting a heart beat rate of a driver; calculating a curve of the heart beat rate average over a time interval of X minutes; calculating a plurality of linear regression slopes of the curve of the heart beat rate average during a time interval of Y minutes; determining an accumulated length of duration during which the calculated linear regression slope values are smaller than the predetermined slope value Z; and determining whether the accumulated length of duration is greater than a time threshold T to generate a drowsiness detecting result, wherein X ranges from 1 to 10, Y ranges from 1 to 10, Z ranges from −0.001 to −0.1, and T ranges from 60 to 600 seconds.

The present disclosure provides another predictive drowsiness alarm method, comprising the following steps: detecting a heart beat rate of a driver; calculating a curve of the heart beat rate average over a time interval of X minutes; calculating a plurality of linear regression slopes of the curve of the heart beat rate average during a time interval of Y minutes; calculating a rate of change of the linear regression slopes in accordance with a time interval, wherein the rate of change is defined as the difference between the linear regression slope during a first time interval and the linear regression slope during a second time interval; and determining whether the rate of change is smaller than a predetermined threshold M of the rate of change to generate a drowsiness detecting result, wherein M ranges from −0.001 to −0.1, X ranges from 1 to 10, and Y ranges from 1 to 10.

The present disclosure provides another predictive drowsiness alarm method, comprising the following steps: detecting a heart beat rate of a driver; calculating a curve of the heart beat rate average over a time interval of X minutes; performing a Fourier transformation on the curve of the heart beat rate average into a plurality of low-frequencies in a Fourier spectrum over a time interval of Y minutes; calculating a rate of change of the low-frequencies in accordance with a time interval, wherein the rate of change is defined as the difference between the low-frequencies during a first time interval and the low-frequencies during a second time interval; and determining whether the rate of change is smaller than a predetermined threshold N of the rate of change to generate a drowsiness detecting result, wherein N is greater than 1, X ranges from 1 to 10, and Y ranges from 1 to 10.

BRIEF DESCRIPTION OF THE DRAWINGS

The accompanying drawings, which are incorporated in and constitute a part of this specification, illustrate embodiments of the disclosure and, together with the description, serve to explain the principles of the invention.

DETAILED DESCRIPTION

In the following description, numerous specific details are set forth. However, it should be understood that embodiments of the invention may be practiced without these specific details. In other instances, well-known methods, structures and techniques have not been shown in detail in order not to obscure an understanding of this description. References to "the present embodiment," "an embodiment," "exemplary embodiment," "other embodiments," etc. indicate that the embodiment(s) of the disclosure so described may include a particular feature, structure, or characteristic, but not every embodiment necessarily includes the particular feature, structure, or characteristic. Further, repeated use of the phrase "in the embodiment" does not necessarily refer to the same embodiment, although it may. Unless specifically stated otherwise, as apparent from the following discussions, it should be appreciated that, throughout the specification, discussions utilizing terms such as "detecting," "sensing," "calculating," "determining," "judging," "transforming," "generating," or the like refer to the action and/or processes of a computer or computing system, or similar electronic computing device, state machine and the like that manipulate and/or transform data represented as physical, such as electronic, quantities, into other data similarly represented as physical quantities.

Figure 1:
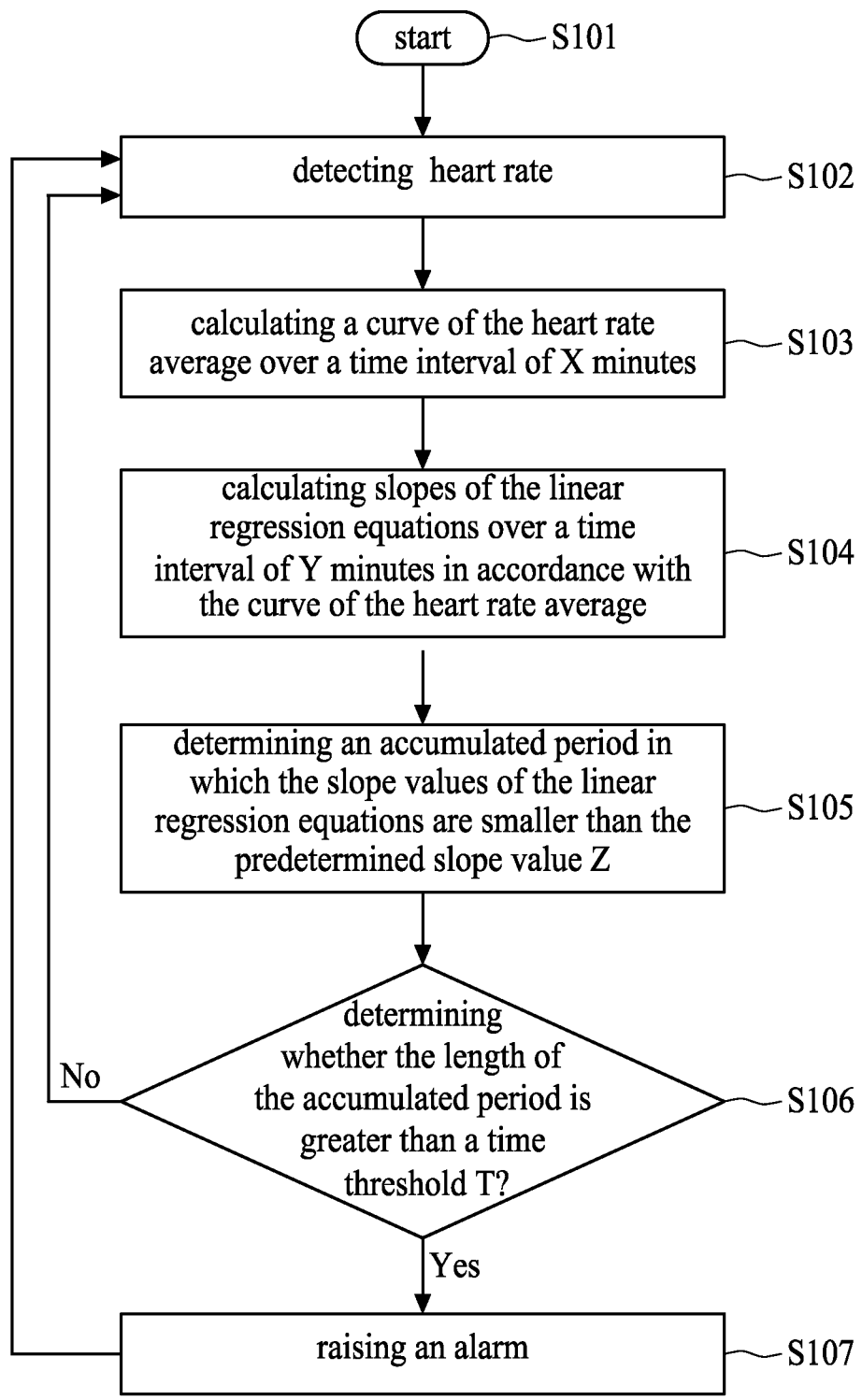
FIG. 1 illustrates a flow chart of one embodiment of a predictive drowsiness alarm method.

FIG. 1 discloses a flow chart of an exemplary embodiment of a predictive drowsiness alarm method in non-contact mode; however, in another exemplary embodiment (not shown), the predictive drowsiness alarm method can be utilized in contact mode. In step S101, the detecting drowsiness method has been initiated. In step S102, the heart beat rate of a driver is sensed or detected (not shown). The heart beat rate refers to the frequency of heartbeats or to the number of heartbeats per unit of time. The heart beat rate of the present embodiment can be measured by an electrocardiographic device in contact mode or be detected by an ultra frequency antenna in non-contact mode. In step S103, a curve of the heart beat rate average over a time interval of X minutes has been calculated. In particular, the heart beat rate average over a time interval of X minutes means that the accumulated heart beat rates during the past X minutes are divided by X minutes to obtain the heart beat rate average at a particular moment. The individual points of the earlier heart beat rate averages are connected to illustrate a curve of the heart beat rate average over a time interval of X minutes, wherein X ranges from 1 to 10. In other words, the curve of the heart beat rate average can be illustrated in accordance with the earlier 1 to 10-minute interval, as shown in FIG. 2.

Referring to FIG. 1, in step S104, a plurality of linear regression slopes of the curve of the heart beat rate average during a time interval of Y minutes can be calculated. In particular, the heart beat rate average can be calculated according to the heart beat rates during the earlier Y-minute intervals. The linear regression slope over a time interval of Y minutes can be calculated in accordance with the heart beat rates during the past Y minutes. Consequently, each of the linear regression slopes can be connected to illustrate a curve (not shown) of the linear regression slopes during a time interval of Y minutes, wherein Y ranges from 1 to 10. In other words, the curve of the linear regression slopes can be illustrated in accordance with the earlier 1 to 10 minute intervals. In step S105, an accumulated length of duration has been determined. The linear regression slope values in the accumulated length of duration are smaller than the predetermined slope value Z. In step S104, after each of the linear regression slopes are calculated, the accumulated length of duration can be determined by adding up the linear regression slopes which are less than the predetermined slope value Z. For instance, if the linear regression slopes from 10:00:00 to 10:00:20 are smaller than the predetermined slope Z, the accumulated length of duration is 20 seconds. However, if the linear regression slope at 10:00:21 is greater than the predetermined slope Z, the accumulated length of duration will be interrupted. In this embodiment, the predetermined slope Z ranges from −0.001 to −0.1. In addition, in another embodiment (not shown), the time interval might range from 1 second to 60 seconds.

As shown in FIG. 1, in step S106, the determination of whether the length of the accumulated length of duration is greater than a time threshold T is performed so as to generate a drowsiness detecting result. In particular, by performing step S105, the accumulated length of duration can be determined. If the accumulated length of duration is 90 seconds, for instance, the time threshold T of 60 seconds is smaller than the length of the accumulated length of duration so as to generate a drowsiness detecting result for raising an alarm. Therefore, the present disclosure can decide to perform the alarm raising step S107 or not based on the drowsiness detecting result. After raising the alarm, the predictive drowsiness detecting method including steps S101 to S107 will be performed again. In another embodiment, if the accumulated length of duration is 90 seconds, for example, the time threshold T of 100 seconds is longer than the accumulated length of duration so as to generate a drowsiness detecting result of not raising the alarm. Subsequently, the predictive drowsiness detecting method will return to step S102 to detect the heart beat rate of the driver and to perform the above-described steps again. Referring to the embodiment shown in FIG. 1, the time threshold T ranges from 60 seconds to 600 seconds.

Figure 2:
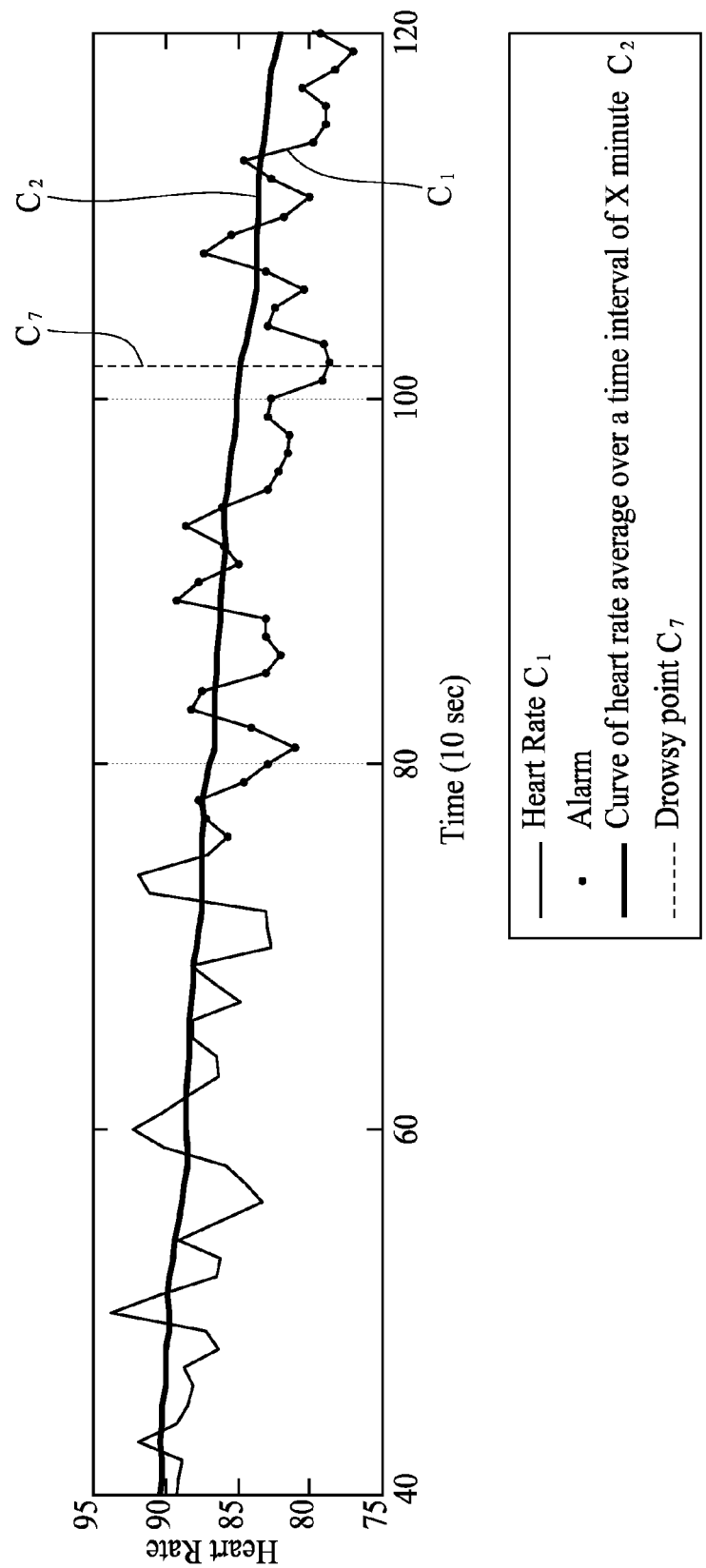
FIG. 2 illustrates a schematic view of one embodiment to raise alarms upon occurrence of a condition.

Referring to FIG. 2 showing the relation between heart beat rate and time in the embodiment, the parameter X is 5, parameter Y is 5, parameter Z is −0.02, and parameter T is 300. As shown in FIG. 2, a curve C1 of the heart beat rate shows a decreasing trend, while a curve C2 of the heart beat rate average during a time interval of X minutes shows the same trend. After the steps of the method shown in FIG. 1 are performed, there are several time points at which alarms are raised as shown in FIG. 2.

Figure 3:
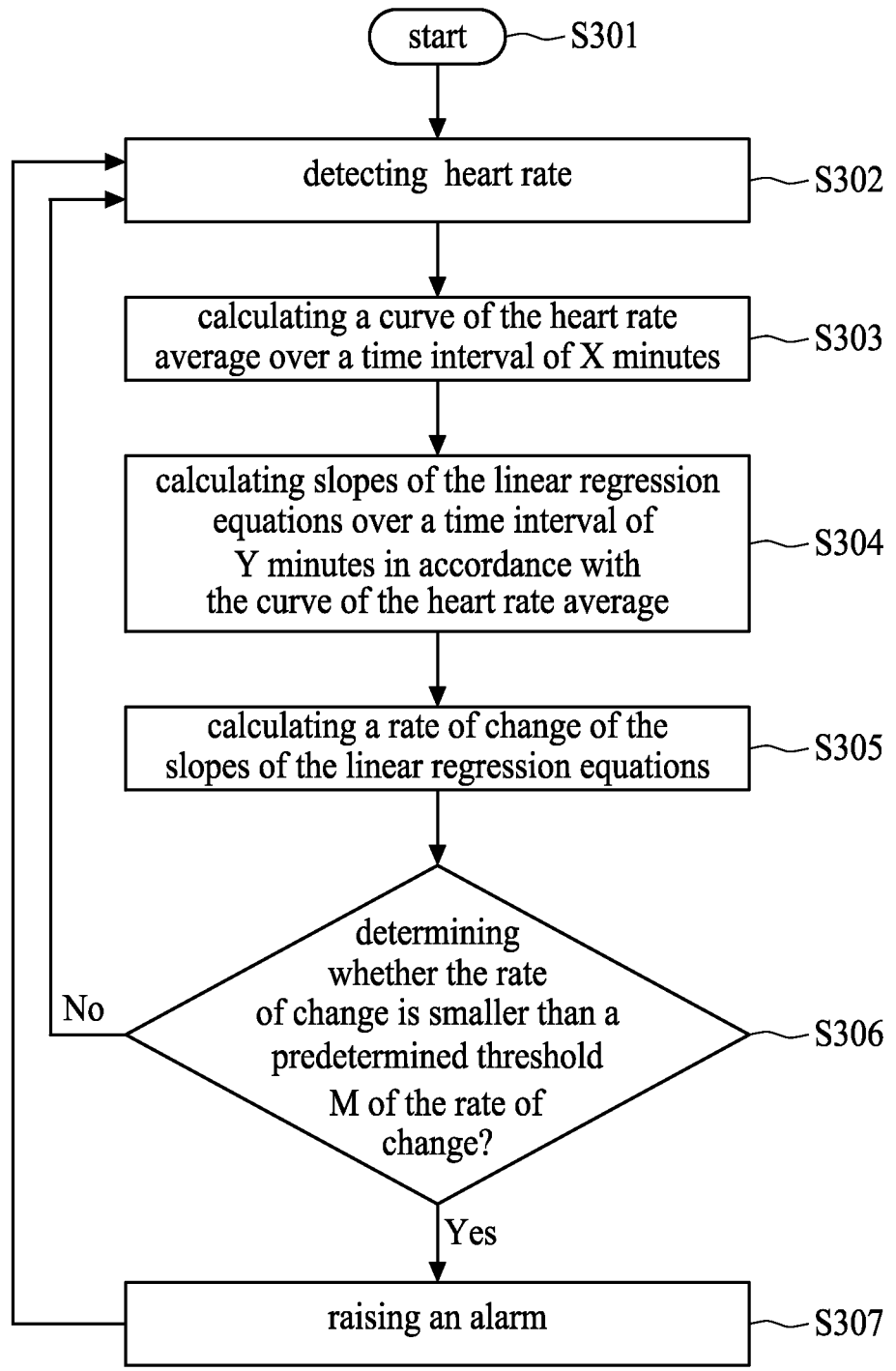
FIG. 3 illustrates a flow chart of another embodiment of the predictive drowsiness alarm method.

FIG. 3 shows another predictive drowsiness detecting method according to another embodiment of the present disclosure. Steps S301, S302, S303 and S304 are similar to the above-mentioned steps S101, S102, S103 and S104, respectively. In step S305, a rate of change of the linear regression slopes is calculated based on a particular time interval. The rate of change is defined as the change between the linear regression slope over the first time interval and the linear regression slope in the second time interval. Particularly, the linear regression slopes in each of the earlier intervals can be calculated and then the rate of change of the linear regression slope can be determined in accordance with the linear regression slopes in each of the earlier time intervals. For example, the linear regression slope in the first interval (from 10:00:10 to 10:00:20) is −3 and the linear regression slope in the second interval (from 10:00:00 to 10:00:10) is −2. Thus, the rate of change is −1 (−3−(−2)=−1). In the embodiment, the time interval is 10 seconds; however, the time interval can be designed in accordance with other requirements. Preferably, the first time interval and the second time interval range from 1 second to 60 seconds.

As shown in FIG. 3, in step S306, a determination whether the rate of change is smaller than a predetermined threshold M of the rate of change is performed so as to generate a drowsiness detecting result. Particularly, the rate of change of the linear regression slopes can be determined by step S305. For instance, if the rate of change is −1 and the predetermined threshold M of the rate of change is −0.1, the rate of change is obviously smaller than the predetermined threshold M. Thus, the drowsiness detecting result according to the above-mentioned calculation will raise an alarm. Therefore, the method of the present disclosure can decide whether to perform the alarm raising step S307 in accordance with the drowsiness detecting result. After raising the alarm, the predictive drowsiness detecting method including steps S301 to S307 will be performed again. In another embodiment, if the rate of change is −0.01, for example, the threshold M of the rate of change of −0.1 is obviously less than the rate of change so as to generate a drowsiness detecting result of not raising an alarm. Subsequently, the predictive drowsiness detecting method will return to step S302 to detect the heart beat rate of the driver and perform the above-mentioned steps again. Referring to the embodiment shown in FIG. 3, the threshold M of the rate of change ranges from −0.001 to −0.1.

Figure 4:
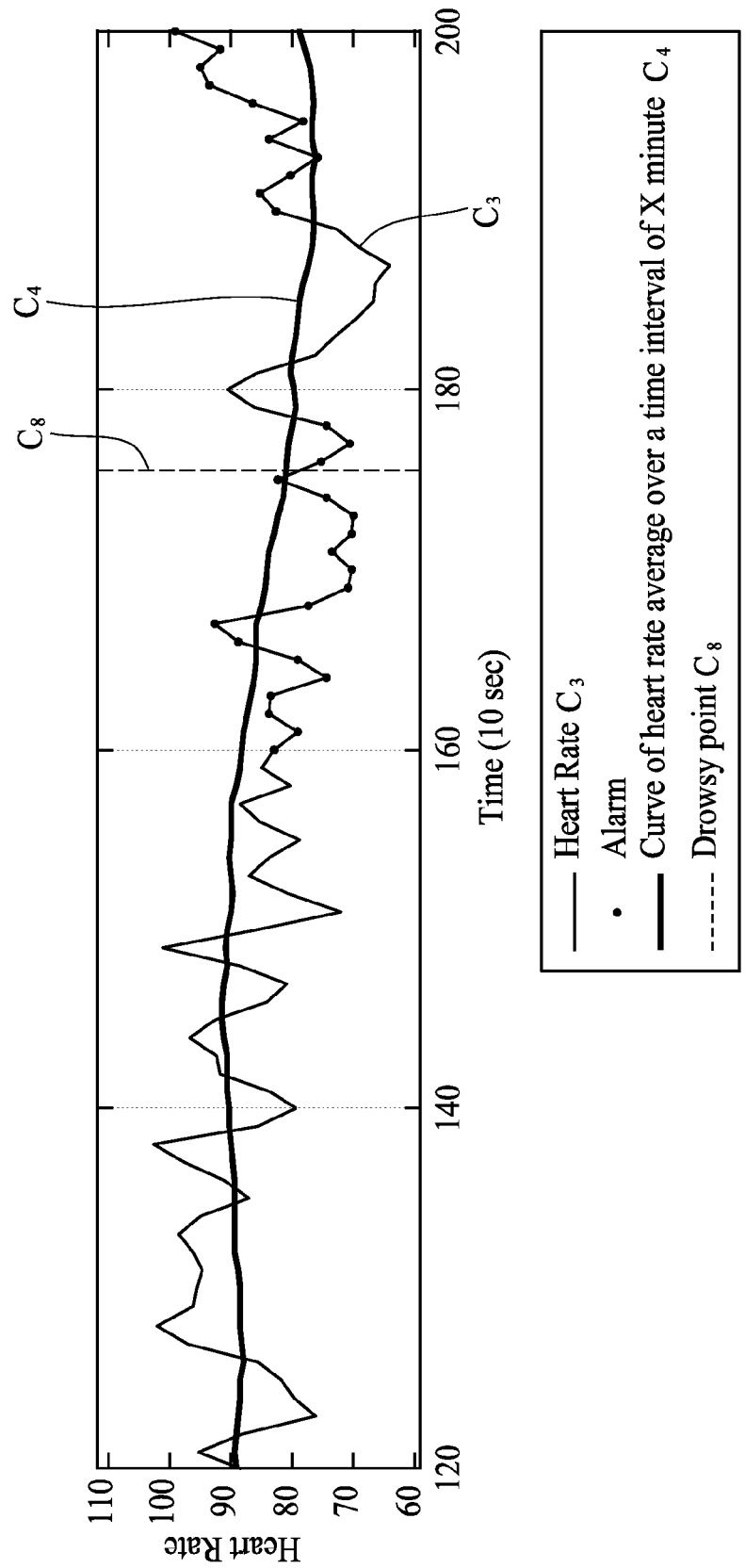
FIG. 4 illustrates a schematic view of another embodiment to raise alarms upon occurrence of another condition.

Referring to FIG. 4 showing the relation between heart beat rate and time in the embodiment, parameter X is 5, parameter Y is 5, and parameter M is −0.01. As shown in FIG. 4, a curve C3 of the heart beat rate shows a decreasing trend; meanwhile, a curve C4 of the heart beat rate average during a time interval of X minutes shows the same trend. After the steps of the method shown in FIG. 3 are performed, there are several time points at which alarms may be raised, as shown in FIG. 4. It is obvious that the time points at which alarms may be raised in the method of FIG. 1 are different from those in the method of FIG. 3.

Figure 5:
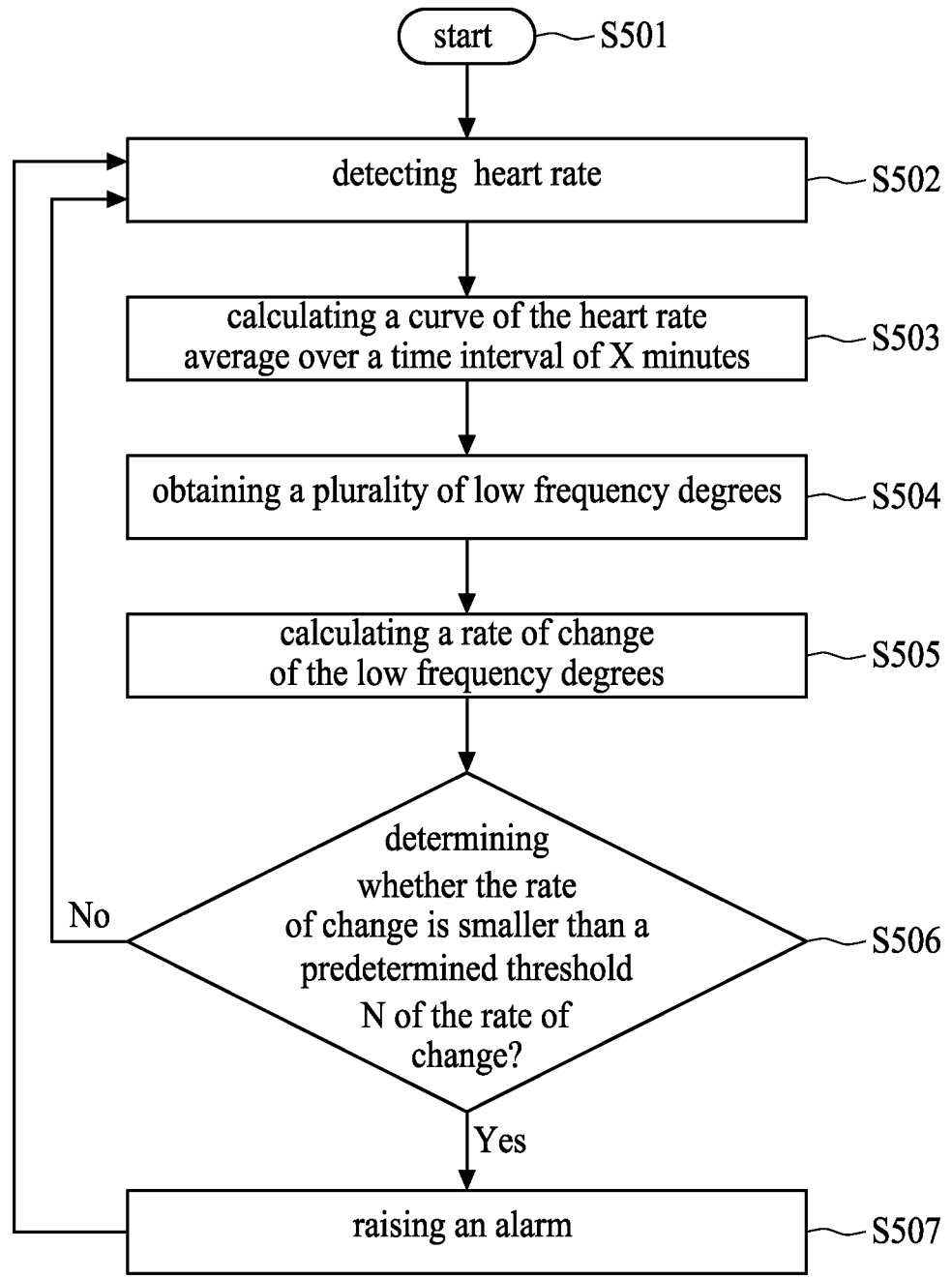
FIG. 5 illustrates a flow chart of another embodiment of the predictive drowsiness alarm method.

FIG. 5 shows another predictive drowsiness detecting method according to another embodiment of the present disclosure. Steps S501, S502, and S503 are similar to the above-mentioned steps S101, S102, and S103, respectively. In step S504, a Fourier transformation of the curve of the heart beat rate average is performed to obtain a plurality of low-frequencies in a Fourier spectrum during a time interval of Y minutes. Particularly, the method of the present disclosure performs a Fourier transformation (N=256) on the curve of the heart beat rate average into a plurality of low-frequencies in the Fourier spectrum. The unit of measure of the low-frequency is times per second. The low-frequencies range in the Fourier spectrum are selected from 0.0005 Hz to 0.005 Hz, 0.0006 Hz to 0.004 Hz, 0.001 Hz to 0.0035 Hz, 0.0018 Hz to 0.0025 Hz, and 0.003 Hz to 0.004 Hz. However, in another embodiment (not shown), the method of the present disclosure can utilize other Fourier transformations to show the low-frequencies in other Fourier spectrums.

In step S505, a rate of change of the low-frequencies is calculated in accordance with a particular time interval. The rate of change is defined as the difference between the low-frequency during the first time interval and the low-frequency during the second time interval. Particularly, the low-frequency in each of the earlier intervals can be calculated and then the rate of change of the low-frequencies can be determined in accordance with the low-frequencies in each of the earlier intervals. For example, the low-frequency in the first time interval (from 10:00:10 to 10:00:20) is 22 and the low-frequency in the second time interval (from 10:00:00 to 10:00:10) is 19. Thus, the rate of change is 3 (22−19=3). In the embodiment, the time interval is 10 seconds; however, the time interval can be designed according to different requirements. Preferably, the first time interval and the second time interval range from 1 second to 60 seconds.

As shown in FIG. 5, in step S506, the determination of whether the rate of change is greater than a predetermined threshold N of rate of change is performed so as to generate a drowsiness detecting result. In particular, by performing step S505, the rate of change of the low-frequencies can be determined. If the rate of change is 3 and the predetermined threshold N of the rate of change is 2, for instance, the rate of change is obviously greater than the predetermined threshold N so as to generate a drowsiness detecting result for raising an alarm. Therefore, the present disclosure can determine whether to perform the alarm raising step S507 in accordance with the drowsiness detecting result. After raising the alarm, the predictive drowsiness detecting method including steps S501 to S507 will be performed again. In another embodiment, if the rate of change is 1 and the predetermined threshold N of rate of change is 3, for example, the rate of change is obviously less than the predetermined threshold N so as to generate a drowsiness detecting result of not raising an alarm. Subsequently, the predictive drowsiness detecting method will return to step S502 to detect the heart beat rate of the driver and to perform the above-mentioned steps again. Referring to the embodiment shown in FIG. 5, the predetermined threshold N is greater than 1.

Figure 6:
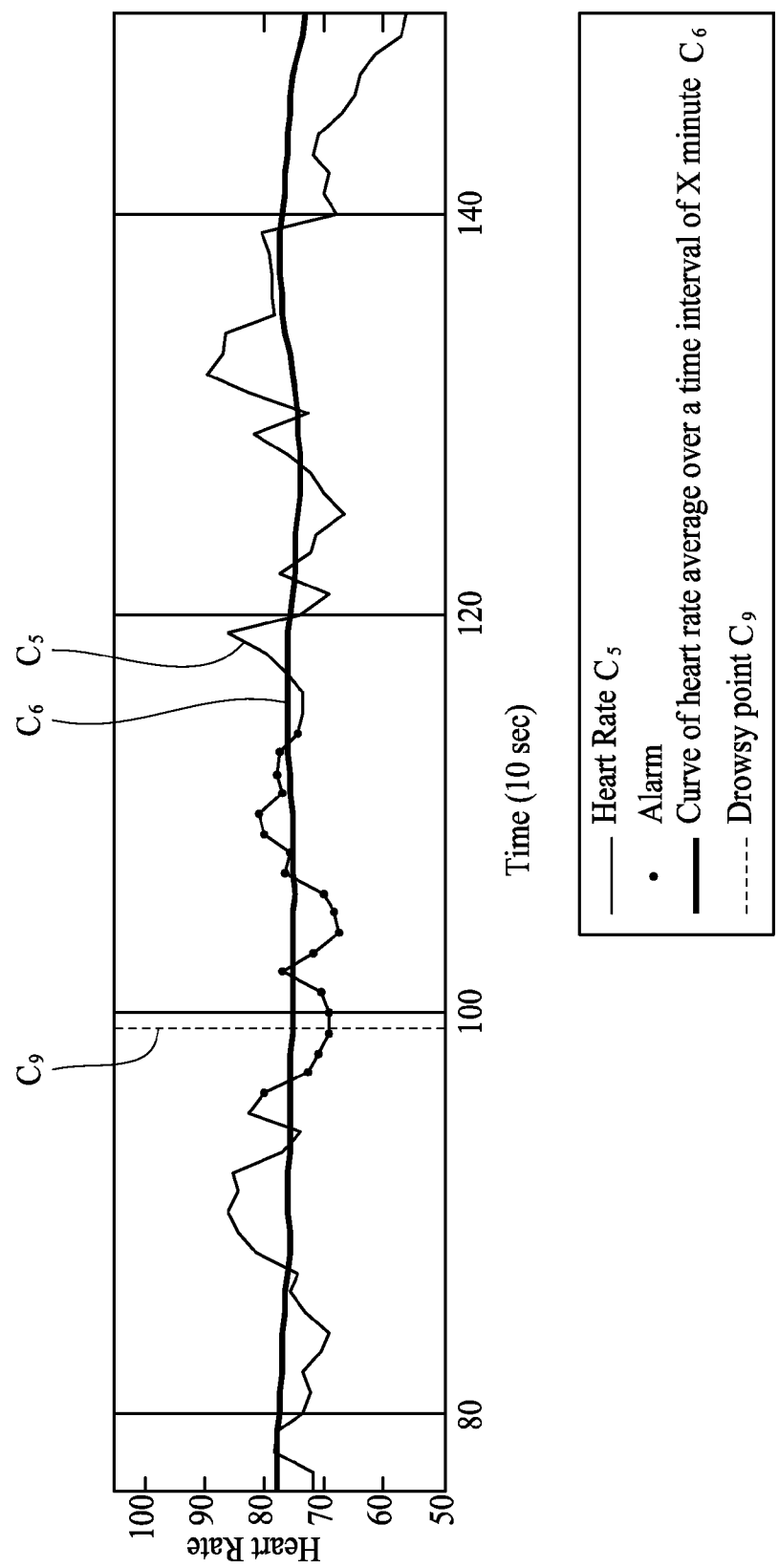
FIG. 6 illustrates a schematic view of another embodiment to raise alarms upon occurrence of another condition.

Referring to FIG. 6, which shows the relation between heart beat rate and time, parameter X is 5, parameter Y is 5, and parameter N is 4. As shown in FIG. 6, a curve $C_5$ of the heart beat rate does not shows a decreasing trend as well as the trends shown in FIGS. 2 and 4; meanwhile, a curve $C_6$ of the heart beat rate average over a time interval of X minutes shows the same trend. After the steps of the method shown in FIG. 5 are performed, there are several time points at which alarms may be raised, as shown in FIG. 6. It is obvious that the time points at which alarms are raised are different among the method of FIG. 1, the method of FIG. 3 and the method of FIG. 5.

Figure 7:
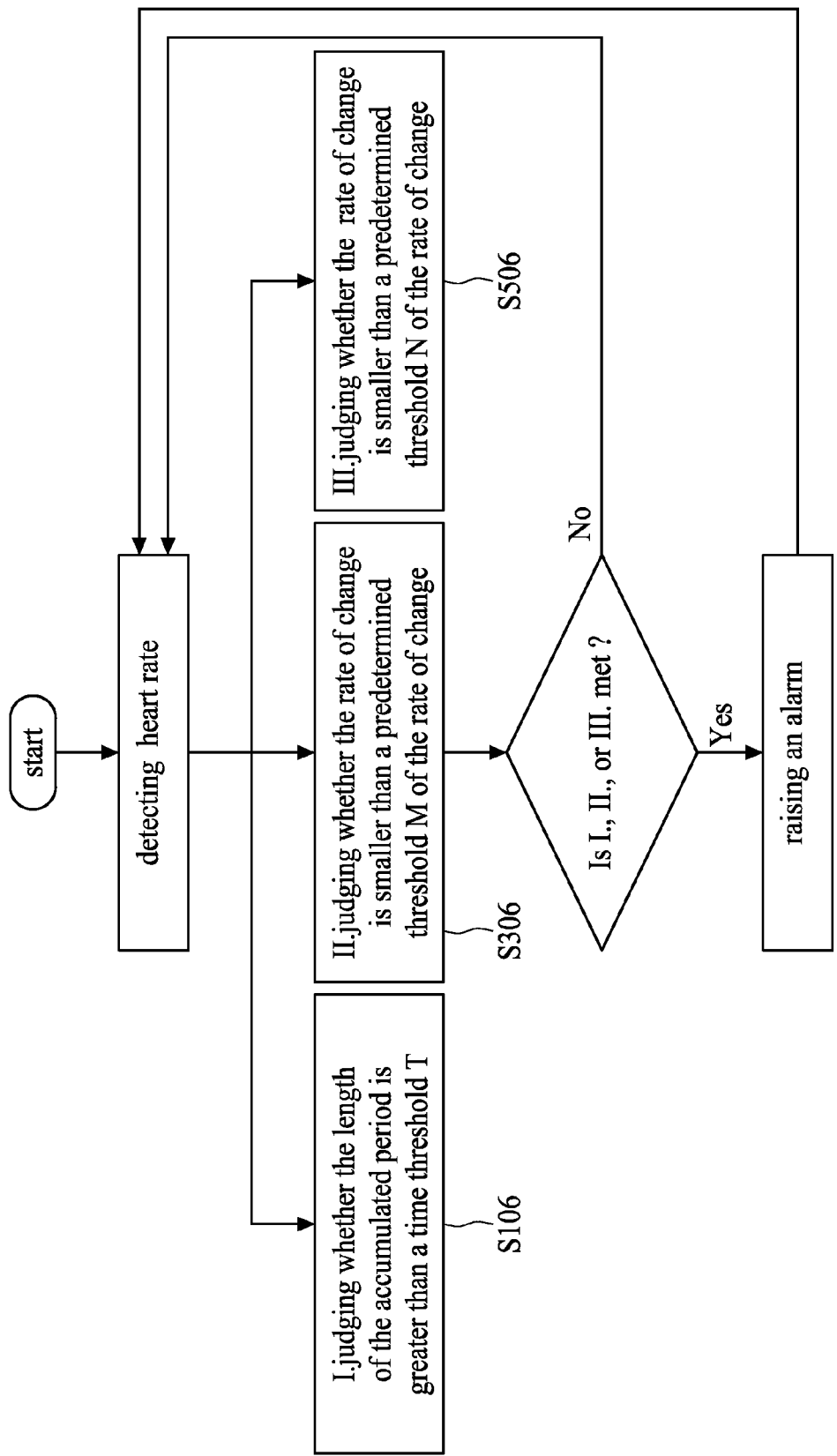
FIG. 7 illustrates a flow chart of another embodiment of the predictive drowsiness alarm method.

The steps of the above-mentioned exemplary embodiment can be partially combined or totally combined to form another embodiment. As shown in FIG. 7, the entire set of steps can be combined. In the embodiment shown in FIG. 7, the steps prior to the judging steps S106, S306, and S506 are not shown. In this embodiment, after the heart beat rate detecting step is performed, a random number is generated to randomly determine whether to perform the steps shown in FIG. 1, the steps shown in FIG. 3, or the steps shown in FIG. 5; however, in another embodiment, the steps in FIG. 1, the steps in FIG. 3, or the steps in FIG. 5 can be implemented in regular order. In the embodiment, when the requirement of steps S106, S306, or S506 is met, the alarms are raised to awake the driver. After the alarms are raised or suppressed, the predictive drowsiness detecting method will detect the heart beat rate of the driver again.

Figure 8:
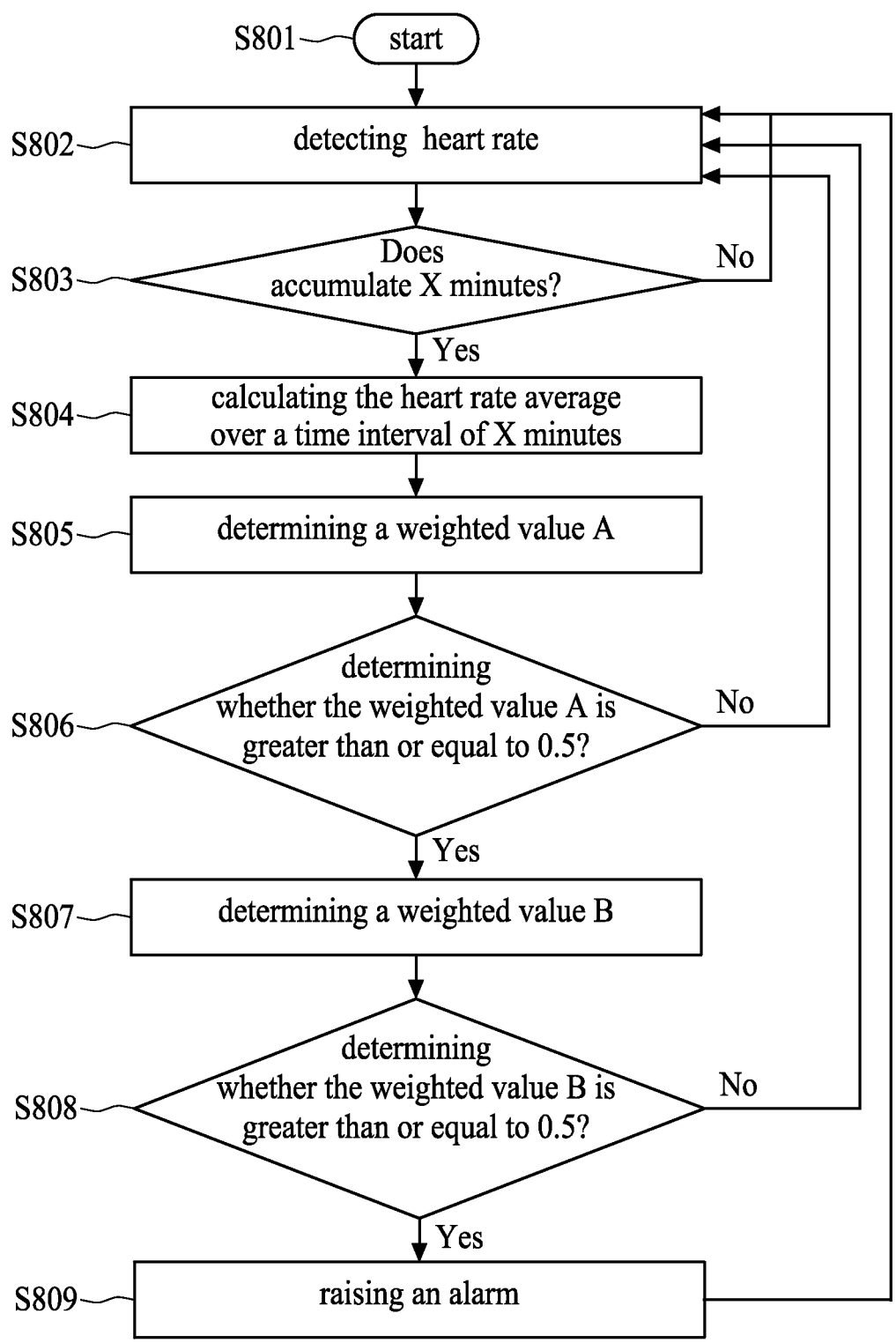
FIG. 8 illustrates a flow chart of another embodiment of the predictive drowsiness alarm method.

In the embodiment shown in FIG. 8, the predictive drowsiness detecting method of the present disclosure can additionally include a weighing concept. Steps S801 and S802 are similar to steps S101 and S102. Moreover, steps S803 and S804 serve to accumulate the detecting period of X minutes and calculate the heart beat rate over a time interval of X minutes and the heart beat rate average, similar to the functions performed in step S103. In step S804, a plurality of linear regression slopes are calculated. Such linear regression slopes refer to individual weighted values A0 in accordance with the accumulated length of duration of the different predetermined slopes Z. For instance, if the accumulated length of duration for which the linear regression slope is less than the predetermined slope (−0.02) exceeds 300 seconds, the weighted value A0 is defined as 0.3; if the accumulated length of duration for which the linear regression slope is less than the predetermined slope (−0.02) exceeds 350 seconds, the weighted value A0 is defined as 0.6; if the accumulated length of duration for which the linear regression slope is less than the predetermined slope (−0.05) exceeds 300 seconds, the weighted value A0 is defined as 1. In this embodiment, the system will retrieve the maximal weighted value A0. For example, if the accumulated length of duration for which the linear regression slope is less than the predetermined slope (−0.05) exceeds 350 seconds, the weighted value A0 is 0.6 instead of 0.3. Furthermore, the weighted value B0 of the linear regression slope can be calculated at the same time. For instance, if the rate of change of the linear regression slopes is less than −0.01 and the accumulated length of duration for which the linear regression slope is less than the predetermined slope (0) exceeds 30 seconds, the weighted value B0 is defined as 0.6. The weighted value A0 and the weighted value B0 can be summed up to determine weighted value A. Thus, step S805 is a determining step of the weighted value A. In step S806, the determination of whether the weighted value A is greater than or equal to the predetermined threshold (0.5) is performed. If the weighted value A is not greater than or equal to the predetermined threshold, the process returns to step S802. If the weighted value A is greater than or equal to the predetermined threshold, step S807 will be implemented. In step S807, another weighted value B is determined. The rate of change of low-frequencies is calculated by step S505 and refers to a corresponding weighted value B. After the weighted value B has been determined in accordance with the rate of change, step S808 is performed. In step S808, it is determined whether the sum of the weighted value A and the weighted value B is greater than or equal to 1. If the sum of the weighted value A and the weighted value B is not greater than or equal to 1, then the process will be returned to step S802. If the sum of the weighted value A and the weighted value B is greater than or equal to 1, the alarms are raised to awake the driver.

The above-described embodiments of the present invention are intended to be illustrative only. Numerous alternative embodiments may be devised by persons skilled in the art without departing from the scope of the following claims. Those skilled in the art may devise numerous alternative embodiments without departing from the scope of the following claims.

What is claimed is:

1. A predictive drowsiness alarm method comprising the following steps:
    detecting a heart beat rate of a driver by an electrocardiographic device or an ultra frequency antenna;
    calculating a curve of a heart beat rate average during a time interval of X minutes, wherein the heart rate average during a time interval of X minutes is accumulated heart beat rates during X minutes divided by X minutes;
    calculating a plurality of linear regression slopes of the curve of the heart beat rate average during a time interval of Y minutes;
    determining an accumulated length of duration during which the calculated linear regression slope values are smaller than a predetermined slope value Z; and
    determining whether the accumulated length of duration is greater than a time threshold T to generate a drowsiness detecting result by using a computer, wherein X ranges from 1 to 10, Y ranges from 1 to 10, Z ranges from −0.001 to −0.1, and T ranges from 60 to 600 seconds.

2. The predictive drowsiness alarm method of claim 1, further comprising a step of determining whether to raise an alarm based on the drowsiness detecting result.

3. The predictive drowsiness alarm method of claim 1, further comprising a step of calculating, based on a time interval, the value of the accumulated length of duration, wherein the time interval ranges from 1 second to 60 seconds.

4. The predictive drowsiness alarm method of claim 3, further comprising a step of calculating, based on the time interval, a rate of change of the linear regression slopes, wherein the rate of change is defined as the difference between the linear regression slope during a first time interval and the linear regression slope during a second time interval.

5. The predictive drowsiness alarm method of claim 4, wherein the first time interval and the second time interval range from 1 to 60 seconds.

6. The predictive drowsiness alarm method of claim 4, further comprising a step of determining whether the rate of change is smaller than a predetermined threshold M of the rate of change to determine the drowsiness detecting result, wherein the threshold M ranges from −0.001 to −0.1.

7. The predictive drowsiness alarm method of claim 3, further comprising a step of performing a Fourier transformation on the curve of the heart beat rate average to obtain a plurality of low-frequencies in a Fourier spectrum over a time interval of Y minutes.

8. The predictive drowsiness alarm method of claim 7, further comprising a step of calculating, based on a time interval, a rate of change of the low-frequencies, wherein the rate of change is defined as the change in the low-frequencies between a first time interval and a second time interval.

9. The predictive drowsiness alarm method of claim 8, wherein the first time interval and the second time interval range from 1 to 60 seconds.

10. The predictive drowsiness alarm method of claim 8, further comprising a step of determining whether the rate of change is greater than a predetermined threshold N of the rate of change to determine the drowsiness detecting result, wherein N is greater than 1.

11. The predictive drowsiness alarm method of claim 8, wherein the low-frequencies range from 0.0005 to 0.005 Hz.

12. The predictive drowsiness alarm method of claim 1, wherein the step of calculating the linear regression slopes of the curve of the heart beat rate average during the time interval of Y minutes, wherein the linear regression slopes are referred to an individual weighing value, and the predictive drowsiness alarm method further comprises a step of determining whether the weighing value is greater than a predetermined threshold to generate the drowsiness detecting result.

* * * * *